(12) United States Patent
Huang et al.

(10) Patent No.: US 10,272,124 B2
(45) Date of Patent: Apr. 30, 2019

(54) USE OF HELMINTHOSTACHYS, UGONINS OR FLAVONE-BASED COMPOUNDS FOR THE TREATMENT OR PREVENTION OF METABOLIC DISEASES

(71) Applicant: National Research Institute of Chinese Medicine, Ministry of Health and Welfare, Taipei (TW)

(72) Inventors: Cheng Huang, Taipei (TW); Keng-Chang Tsai, Taipei (TW); Yu-Ling Huang, Taipei (TW); Ming-Jaw Don, Taipei (TW); Hsiu-Chen Huang, Taipei (TW); Wang-Chuan Chen, Taipei (TW); Hui-Kang Liu, Taipei (TW)

(73) Assignee: NATIONAL RESEARCH INSTITUTE OF CHINESE MEDICINE, MINISTRY OF HEALTH AND WELFARE, Taipei (TW)

( * ) Notice: Subject to any disclaimer, the term of this patent is extended or adjusted under 35 U.S.C. 154(b) by 86 days.

(21) Appl. No.: 15/485,985

(22) Filed: Apr. 12, 2017

(65) Prior Publication Data

US 2017/0348367 A1    Dec. 7, 2017

(30) Foreign Application Priority Data

Jun. 6, 2016    (TW) .............................. 105117782 A

(51) Int. Cl.
*A61K 36/12* (2006.01)
*A61K 31/352* (2006.01)

(52) U.S. Cl.
CPC ............ *A61K 36/12* (2013.01); *A61K 31/352* (2013.01); *A61K 2236/00* (2013.01)

(58) Field of Classification Search
CPC .. A61K 2236/00; A61K 31/352; A61K 36/11; A61K 36/12; A61P 3/00; A61P 11/00
See application file for complete search history.

(56) References Cited

PUBLICATIONS

Parveen R, et al "A rewiew on Antidiabetic Angiospermic plants from the regions of Uttarakhand, India" IOSR Journal of Pharmacy (e)-ISSN: 2250-3013, (p)-ISSN: 2319-4219, vol. 6,iss.10,ver.1, (Oct. 2016), pp. 14-61. (Year: 2016).*
Alqasounni SI, et al "Screening of some Traditionally Used Plants for Their Hepatoprotective Effect" Phytochemicals as Nutraceuticals—Global Approaches to Their Role in Nutrition and Health, Dr Venketeshwer Rao (Ed.), ISBN: 978-953-51-0203-8, Mar. 23, 2012, chapter 14, pp. 255-278. (Year: 2012).*
Suja SR, et al "Evaluation of Antihepatotoxic Potential of Helminthostachys zeylanica (Linn.) Hook. f., a Medicinal Fern against Ethanol Induced Liver Damage: In vitro and In vivo Studies " American Journal of Experimental Biology (May 17, 2014) vol. 1 No. 1 pp. 16-30. (Year: 2014).*
Wu KC, et al "Ugonin M, a Helminthostachys zeylanica Constituent, Prevents LPS-Induced Acute Lung Injury through TLR4-Mediated MAPK and NF-κB Signaling Pathways" Molecules, Apr. 1, 2017, 22, 573, 15 pages; doi:10.3390/molecules22040573. (Year: 2017).*
Wu KC, et al "Quality Control of the Root and Rhizome of Helminthostachys zeylanica (Daodi-Ugon) by HPLC Using Quercetin and Ugonins as Markers" Molecules, Jul. 5, 2017, 22(7), 1115, 10 pages; https://doi.org/10.3390/molecules22071115. (Year: 2017).*
Hsieh HL, et al "Evaluation of Anti-Inflammatory Effects of Helminthostachys zeylanica Extracts via Inhibiting Bradykinin-Induced MMP-9 Expression in Brain Astrocytes" Mol Neurobiol, 2016 (pub online Nov. 2, 2015), 53, pp. 5995-6005; doi 10.1007/s12035-015-9511-9. (Year: 2016).*
Fitrya, et al "Ugonin J Flavonoid from Tunjuk Langit (*Helminthostachys zeylanica* Linn.) Root Extract" Indo. J. Chem., 2010, 10 (2), pp. 233-238. (Year: 2010).*
Liao W-Y, et al "Cyclohexylmethyl Flavonoids Suppress Propagation of Breast Cancer Stem Cells via Downregulation of NANOG" Evidence-Based Complementary and Alternative Medicine (ECAM), Apr. 4, 2013 (pub. online), vol. 2013, Article ID 170261, 14 pp.; doi:10.115. (Year: 2013).*
Huang YC, et al ("Anti-inflammatory flavonoids from the rhizomes of Helminthostachys zeylanica" J. Natural Products,2009,72(7), pp. 1273-1278. (Year: 2009).*
Suja SR, et al "Evaluation of Antihepatotoxic Potential of Helminthostachys zeylanica (Linn.) Hook. f., a Medicinal Fern against Ethanol Induced Liver Damage: In vitro and In vivo Studies" American Journal of Experimental Biology (AJEB), May 17, 2014, 1(1), pp. 16-30. (Year: 2014).*
Fern K, et al "Helminthostachys zeylanica", Useful Tropical Plants Database, 2014, ret. Oct. 2018, <url: tropical.theferns.info/viewtropical.php?id= Helminthostachys+zeylanica>, 2 pages. (Year: 2014).*
NCBI-NLM "Ugonin L " PubChem (CID: 10365741 ), <https://pubchem.ncbi.nlm.nih.gov/compound/10365741#section=Substances-by-Category?>, accessed online Oct. 25, 2018, 11 pages (Year: 2018).*

(Continued)

*Primary Examiner* — Aaron J Kosar
(74) *Attorney, Agent, or Firm* — Muncy, Geissler, Olds & Lowe, P.C.

(57) ABSTRACT

Disclosed is a use of *Helminthostachys zeylanica*, ugonins or compounds of formula (I) for the treatment or prevention of metabolic diseases comprising at least one selected from metabolic syndrome, excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease, hyperglycemia, hyperinsulinemia, diabetes mellitus type 2, insulin resistance, insulin disorder, impaired glucose tolerance and a combination thereof.

12 Claims, 10 Drawing Sheets

(56) References Cited

PUBLICATIONS

Suja et al., "Evaluation of hepatoprotective effects of *Helminthostachys zeylanica* (L.) Hook against carbon tetrachloride-induced liver damage in Wistar rats," Journal of Ethnopharmacology, vol. 92 (2004) pp. 61-66.

Ming et al., "Study on Hypoglycemic Effect and Mechanism of Total Flavonoids of Propolis in STZ Diabetic Rats," Journal of Chinese Medicinal Materials, vol. 37, No. 9, Sep. 2014, 10 pages.

Huang et al., "Anti-inflammatory Flavonoids from the Rhizomes of *Helminthostachys zeylanica*," J. Nat. Prod., vol. 72, 2009, pp. 1273-1278.

\* cited by examiner

USE OF HELMINTHOSTACHYS, UGONINS OR FLAVONE-BASED COMPOUNDS FOR THE TREATMENT OR PREVENTION OF METABOLIC DISEASES

CROSS-REFERENCE TO RELATED APPLICATION

This Application claims priority of Taiwan Patent Application No. 105117782, filed on Jun. 6, 2016, the entirety of which is incorporated by reference herein and made a part of this specification.

BACKGROUND

1. Field of the Invention

The present disclosure relates to a novel use of Chinese herbal medicines in the treatment of metabolic diseases and more particularly to the use of *Helminthostachys zeylanica*, ugonins isolated therefrom and compounds of formula (I) in the treatment or prevention of metabolic diseases.

2. Description of Related Art

It has been known that obesity and insulin disorder are correlated with various diseases, such as cardiovascular disease, diabetes mellitus type 2, fatty liver, etc., and these diseases are highly associated to abnormal lipid metabolism or abnormal carbohydrate metabolism.

For example, fatty liver refers to the initial stage of a non-alcoholic fatty liver disease, which is a common metabolic syndrome primarily caused by unbalanced lipid metabolism. Abundant clinical and experimental evidence indicates that fatty liver leads to cirrhosis and results in health problems such as steatohepatitis and liver necrosis.

Currently, diet control and exercise are believed to be the most effective measures for the prevention and treatment of the aforesaid diseases and various other metabolic diseases, and other existing therapies are still unsatisfactory.

SUMMARY

An object of the present disclosure is to provide a method of using *Helminthostachys zeylanica* for the treatment or prevention of a metabolic disease and more particularly to disclose the use of *Helminthostachys zeylanica* in the preparation of medicaments useful for the treatment or prevention of metabolic diseases.

Another object of the present disclosure is to provide a method of using ugonin(s) for the treatment or prevention of a metabolic disease and more particularly to disclose the use of ugonin(s) in the preparation of medicaments useful for the treatment or prevention of metabolic diseases.

Still another object of the present disclosure is to provide a method of using a compound of formula (I) or its pharmaceutically acceptable salt for the treatment or prevention of a metabolic disease and more particularly to disclose the use of a compound of formula (I) or its pharmaceutically acceptable salt in the preparation of medicaments useful for the treatment or prevention of metabolic diseases. Definition of radicals and functional groups in formula (I) will be given below.

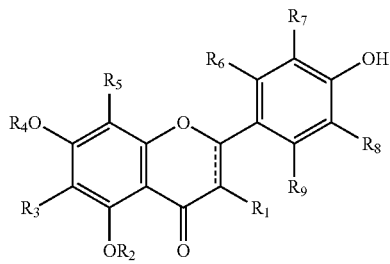

More particularly, said medicaments may comprise extracts of *Helminthostachys zeylanica*, for example but not limited to rhizome extracts of *Helminthostachys zeylanica*, such as alcoholic extracts of the rhizome portion of *Helminthostachys zeylanica*, such as an ethanol extract.

The metabolic diseases may be roughly divided into three classes: metabolic syndrome, lipid metabolism disorder and carbohydrate metabolism disorder, wherein lipid metabolism disorder is selected from the group consisting of excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease, and a combination thereof, and wherein carbohydrate metabolism disorder is selected from the group consisting of hyperglycemia, hyperinsulinemia, diabetes mellitus type 2, insulin resistance, insulin disorder, impaired glucose tolerance and a combination thereof.

DESCRIPTION OF THE EMBODIMENTS

Figure 1A:
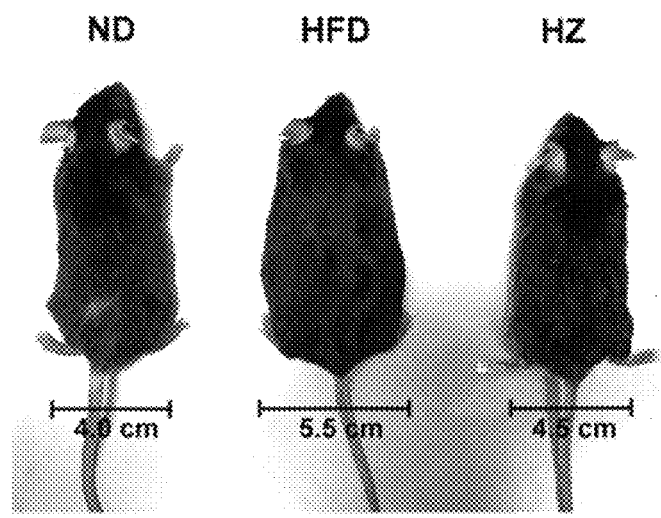
FIG. 1A shows changes in body shape and waistline of mice.

The present disclosure primarily pertains to the unexpected discovery of the efficacy of *Helminthostachys zeylanica* on the treatment or prevention of metabolic diseases.

*Helminthostachys zeylanica* is a common anti-inflammatory herbal medicine used in Taiwan as well as in China, Southeast Asia, India, etc.

As used herein, "*Helminthostachys zeylanica*" refers to and covers a plant of genus *Helminthostachyaceae* with Binomial name *Helminthostachys zeylanica* (L.) Hook, abbreviated as HZ, which is also known as Ding-Di-U-Gon.

Unless otherwise specified, *Helminthostachys zeylanica* as used in the present disclosure comprises the whole plant of *Helminthostachys zeylanica*, any part thereof or a mixture of multiple parts thereof. *Helminthostachys zeylanica* may be used in the form of raw and fresh plant or one or more parts thereof, dried matters, ground matters, decocted matters, extract or any form suitable for administration to a recipient or subject including human and other animals, such as oral formulation.

For example, *Helminthostachys zeylanica* may be used as an extract, such as a condensed product or dried product, containing bioactive substances such as ugonins. Unless otherwise specified, extraction method, extraction solvent, extraction component or extraction type is not particularly limited and may be selected by a person skilled in the art according to the need. For example, the rhizome part or other parts of *Helminthostachys zeylanica* may be processed to prepare an ethanol extract.

In one embodiment, "treatment" refers to a scheme, process or therapy useful for human and non-human animals, including alleviating, curing or preventing the disease or symptom. Unless otherwise specified, treatment may be performed by administering to a recipient in need thereof a therapeutically effective amount of *Helminthostachys zeylanica*, its extract, ugonins, or compound of formula (I) or its pharmaceutically acceptable salt. Therapeutically effective amount may be for example a daily dose of at least 3 g of Chinese patent medicine prepared according to any known method or a daily dose of at least 37.5 g of Chinese medicine decoction prepared according to any known method, wherein Chinese patent medicine and Chinese medicine decoction have their respective ordinary meaning as known in the art.

In one embodiment, the term "treatment" refers to obtaining desired pharmacological effects and/or physiological effects, including both prophylactic and preventative measures for completely or partially preventing a disease or symptom and therapeutic treatment for completely or partially curing a disease or providing counteracting effect against disease development.

As used herein, the term "treatment" encompasses any treatment for mammals particularly humans and includes: (a) prevention of a disease in a predisposed individual before the individual is diagnosed with the disease; (b) inhibition of the development of a disease; and (c) alleviation or regression of a disease.

"Therapeutically effective amount" refers to an amount that is sufficient to achieve treatment or prevention of a disease or disorder in an individual by using the aforesaid *Helminthostachys zeylanica*, extract thereof, ugonin, compound of formula (I) or its pharmaceutically acceptable salt or pharmaceutical composition. A composition of compounds is preferably a synergistic composition as known in the art, which possesses better efficacy when compounds are co-administered than when they are administered individually. Generally, synergistic effect may be observed when compounds are used at a sub-optimal concentration. In contrast to the effect of individual components, synergistic effect may reduce cellular toxicity, increase activity or obtain other beneficial results of the composition.

In one embodiment, "prevention" or any grammatical variation thereof refers to prophylactic measures advantageous to human or non-human animals; prevention may be performed before or during the onset or development of diseases or symptoms.

As used herein, prevention and treatment may encompass various measures taken in order to treat, mitigate, inhibit, alleviate, regulate, relieve or control diseases or symptoms.

As used herein, metabolic disease includes but not limited to innate and acquired metabolic diseases or disorders, such as metabolic syndrome, lipid metabolism disorder or carbohydrate metabolism disorder.

Metabolic syndrome is generally associated to the following risk factors: (1) abdomen obesity, such as waist circumference $\geq 90$ cm for men and $\geq 80$ cm for women; (2) high blood pressure, such as systolic blood pressure (SBP) $\geq 130$ mmHg and diastolic blood pressure (DBP) $\geq 85$ mmHg; (3) high blood glucose, such as fasting glucose (FG) $\geq 100$ mg/dl; (4) high density lipoprotein cholesterol (HDL-C) $<40$ mg/dl for men and $<50$ mg/dl for women; and/or (5) high triglyceride (TG) such as $\geq 150$ mg/dl.

Lipid metabolism disorder includes metabolic diseases caused by eating disorder (e.g. high fat or high sugar diet) and non-eating disorder; examples of lipid metabolism disorder include, but not limited to, excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease and a combination thereof.

Carbohydrate metabolism disorder includes metabolic diseases caused by eating disorder (e.g. high fat or high sugar diet) and non-eating disorder; examples of carbohydrate metabolism disorder include, but not limited to, hyperglycemia, hyperinsulinemia, diabetes mellitus type 2, insulin resistance, insulin disorder, impaired glucose tolerance and a combination thereof.

Another aspect of the present disclosure relates to the unexpected discovery of the efficacy of ugonins on the treatment or prevention of metabolic diseases. Ugonins may be isolated from for example *Helminthostachys zeylanica* or obtained from other sources; alternatively, ugonins may also be obtained by chemical synthesis.

As discovered by the inventors, ugonins demonstrate significant efficacy on diet-induced metabolic diseases and may be used for preventing, treating, inhibiting or alleviating various metabolic diseases, therefore showing high potential in the development of drugs, plant-derived drugs, functional foods or healthy foods. For example, plants containing various ugonins, such as *Helminthostachys zeylanica*, may be extracted to obtain an extract containing two or more ugonins. To enhance or enrich the content of specific one or more ugonins, extraction conditions and known factors may be adjusted according to the needs.

Unless otherwise specified, ugonins as used herein include at least 21 different types, from ugonin A to ugonin U, of which ugonin J, ugonin K, ugonin L, ugonin M, ugonin O, and ugonin T are preferred, and a mixture of any two or more ugonins is more preferred.

According to the in vitro and in vivo experiments, it is believed that ugonins may regulate the activity of any one or more of the following biomolecules: PPAR-γ (peroxisome proliferator-activated receptor gamma), Akt (protein kinase B), AMPK (AMP-activated protein kinase), ACC (acetyl-CoA carboxylase), SREBP1 (sterol regulatory element-binding protein 1), FAS (fatty acid synthase), FOXO1 (forkhead box protein O1), CPT1 (carnitine palmitoyltransferase I) or ATGL (adipose triglyceride lipase); therefore, ugonins may be useful for preparing a medicament for the prevention or treatment of metabolic diseases mediated or regulated by PPAR-γ, Akt, AMPK, ACC, SREBP1, FAS, FOXO1, CPT1 or ATGL, including but not limited to metabolic syndrome, excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease, hyperglycemia, hyperinsulinemia, diabetes mellitus type 2, insulin resistance, insulin disorder, impaired glucose tolerance and a combination thereof.

Still another aspect of the present disclosure relates to the use of a compound of formula (I) or its pharmaceutically acceptable salt for the treatment or prevention of metabolic diseases comprising at least one of metabolic syndrome, excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease, hyperglycemia, hyperinsulinemia, diabetes mellitus type 2, insulin resistance, insulin disorder, impaired glucose tolerance and a combination thereof.

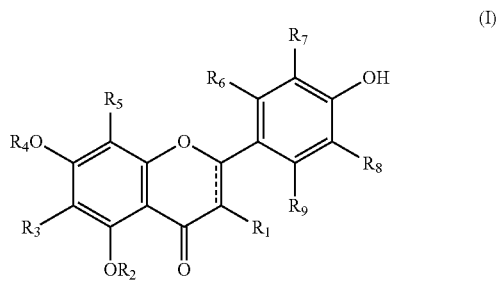

(I)

⫶⫶ represents a single bond or a double bond; $R_1$ is selected from H, OH and $(OC_1-C_6)$alkyl, or $R_1$ and $R_9$ form an oxygen-containing heterocyclic ring; $R_2$ is H, or $R_2$ and $R_3$ form an oxygen-containing heterocyclic ring; $R_3$ is selected from H or substituted or unsubstituted $(C_1-C_6)$ alkylene$(C_3-C_6)$cyclohydrocarbyl, or $R_3$ and $R_2$ form an oxygen-containing heterocyclic ring, or $R_3$ and $R_4$ form an oxygen-containing heterocyclic ring; $R_4$ is selected from H and $(C_1-C_6)$alkyl, or $R_4$ and $R_3$ form an oxygen-containing heterocyclic ring, or $R_4$ and $R_5$ form an oxygen-containing heterocyclic ring; $R_5$ is selected from H and $(C_1-C_6)$alkyl-substituted $(C_2-C_6)$alkenyl, or $R_5$ and $R_4$ form an oxygen-containing heterocyclic ring; $R_6$ is selected from H and substituted or unsubstituted $(C_1-C_6)$alkylene$(C_3-C_6)$cyclohydrocarbyl, or $R_6$ and $R_7$ form an oxygen-containing heterocyclic ring; $R_7$ is selected from H, OH and $(OC_1-C_6)$ alkyl, or $R_7$ and $R_6$ form an oxygen-containing heterocyclic ring; $R_8$ is selected from H and OH; and $R_9$ is H, or $R_9$ and $R_1$ form an oxygen-containing heterocyclic ring.

As used herein, a "pharmaceutically acceptable salt" refers to an ionic compound, where a nontoxic parent compound is modified to prepare its acidic salt or basic salt. One example of the pharmaceutically acceptable salt comprises an inorganic salt or organic salt containing amine as the basic group, an alkali metal salt or organic salt containing carboxylic acid as the acidic group, and analogs thereof. Pharmaceutically acceptable salts include known nontoxic salts and quaternary ammonium salts of parent compounds formed by nontoxic inorganic or organic acids.

Said salts may be derived from hydrochloric acid, hydrobromic acid, hydriodic acid, sulfuric acid, sulfamic acid, phosphoric acid, nitric acid or other similar inorganic acids. For salts obtained from an organic acid, examples of the organic acid comprise acetic acid, 2-acetoxybenzoic acid, ascorbic acid, benzenesulfonic acid, benzoic acid, citric acid, ethanesulfonic acid, ethane disulfonic acid, foimic acid, fumaric acid, gentisinic acid, glucuronic acid, gluconic acid, glutamic acid, glycolic acid, hydroxymaleic acid, isethionic acid, isonicotinic acid, lactic acid, maleic acid, malic acid, methanesulfonic acid, oxalic acid, pantothenic acid, phenylacetic acid, propionic acid, salicylic acid, sulfanilic acid, p-toluenesulfonic acid, stearic acid, succinic acid, tartaric acid, bitartaric acid, and the like; certain compounds can form pharmaceutically acceptable salts with various amino acids.

The pharmaceutically acceptable salts of the compounds as described herein can be synthesized from the parent compound, which contains a basic or acidic moiety, by conventional chemical methods. Generally, such salts can be prepared by reacting the free acid or base forms of these compounds with a stoichiometric amount of the suitable base or acid in water, in an organic solvent, or in a mixture thereof; useful non-aqueous media may be for example ether, ethyl acetate, ethanol, isopropanol, or acetonitrile.

One or more compounds of formula (I) or their pharmaceutically acceptable salts may be present in the form of a pharmaceutical composition, which is a composition or combination comprising a compound of formula (I) or its pharmaceutically acceptable salt and comprising a pharmaceutically acceptable carrier, such as a diluent, a vehicle or an excipient for co-administration. The carrier may be a liquid (e.g. water and oil), brine or the like. Other ingredients may also be used, such as promoters, stabilizers, thickeners, lubricants, colorants, and the like. As used herein, a pharmaceutically acceptable carrier or excipient comprises, but not limited to, fillers, binders, disintegrants, lubricants and any other ingredient useful for administering the aforesaid compounds or their pharmaceutically acceptable salts to a recipient.

As used herein, where a numerical limit or range is stated, the endpoints are included; also, all values and subranges within a numerical limit or range are specifically included as if explicitly written out. For example, $C_1-C_4$ shall include $C_1$, $C_2$, $C_3$, and $C_4$, as well as $C_1-C_2$, $C_1-C_3$, $C_1-C_4$, $C_2-C_3$, $C_2-C_4$, and $C_3-C_4$.

As used herein, $(OC_1-C_6)$alkyl represents $(C_1-C_6)$alkoxy group.

The term "alkyl" refers to a hydrocarbonyl group containing normal, secondary, tertiary or cyclic carbon atoms. Examples are methyl, ethyl, 1-propyl, 2-propyl, 1-butyl, 2-methyl-1-propyl (iso-butyl), 2-butyl (sec-butyl), 2-methyl-2-propyl (tert-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. The alkyl can be a monovalent hydrocarbon radical or a divalent hydrocarbon radical (i.e., alkylene).

The term "alkoxy" refers to the group alkyl-O—, where alkyl is defined above. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy and the like.

As used herein, an oxygen-containing heterocyclic ring refers to a cyclic structure or radical with an oxygen heteroatom, such as an oxygen-containing five-membered heterocyclic ring, an oxygen-containing six-membered heterocyclic ring, an oxygen-containing seven-membered heterocyclic ring, and the like. The aforesaid oxygen-containing heterocyclic ring may be an independent (non-fused) group or radical or combined with other cyclic groups (fused).

As used herein, cyclohydrocarbyl may be a cyclic hydrocarbyl with multiple carbon atoms, such as a cycloalkyl or cycloalkenyl, which may comprise a monocyclic ring or a fused ring. Examples of cycloalkyl comprise a monocyclic structure, such as cyclopropyl, cyclobutyl, cyclopentyl, cyclohexyl, etc.

Unless otherwise specified, compounds of formula (I) may be present as any one of different stereoisomers. In other words, compounds of formula (I) according to the present disclosure may comprise stereoisomers with different atomic arrangement, such as enantiomers and diastereomers, wherein an asymmetric substituted carbon atom forms a chiral center. Symbols R and S represent the configuration of substituents of the chiral carbon atom.

In one embodiment, $R_1$ of compounds of formula (I) is selected from H, OH and $(OC_1-C_3)$alkyl.

In one embodiment, $R_2$ of compounds of formula (I) is H.

In one embodiment, $R_3$ of compounds of formula (I) is selected from H or substituted or unsubstituted $(C_1-C_3)$ alkylene($C_5-C_6$)cyclohydrocarbyl.

In one embodiment, $R_4$ of compounds of formula (I) is selected from H and $(C_1-C_3)$alkyl, or $R_4$ and $R_5$ form an oxygen-containing heterocyclic ring.

In one embodiment, $R_5$ of compounds of formula (I) is selected from H and $(C_1-C_3)$alkyl$(C_2-C_4)$alkenyl.

In one embodiment, $R_6$ of compounds of formula (I) is H.

In one embodiment, $R_7$ of compounds of formula (I) is selected from H, OH and $(OC_1-C_3)$alkyl.

In one embodiment, $R_8$ of compounds of formula (I) is selected from H and OH.

In one embodiment, $R_9$ of compounds of formula (I) is H.

Particularly, examples of compounds of formula (I) comprise any one or more of the following:

2-(3,4-dihydroxyphenyl)-5-hydroxy-12,12-dimethyl-8,8a,9,10,11,12,12a,13-octahydro-4H-benzo[5,6]oxepino[2,3-h]chromen-4-one;

5-hydroxy-2-(4-hydroxy-3-methoxyphenyl)-12,12-dimethyl-8,8a,9,10,11,12,12a,13-octahydro-4H-benzo[5,6]oxepino[2,3-h]chromen-4-one;

5-hydroxy-2-(4-hydroxyphenyl)-3-methoxy-8,9,9-trimethyl-8,9-dihydro-4H-furo[2,3-h]chromen-4-one;

5-hydroxy-2-(4-hydroxyphenyl)-8,9,9-trimethyl-2,3,8,9-tetrahydro-4H-furo[2,3-h]chromen-4-one;

(R)-5,7-dihydroxy-2-(4-hydroxyphenyl)-8-(2-methylbut-3-en-2-yl)chroman-4-one;

3,5-dihydroxy-2-(4-hydroxyphenyl)-8,9,9-trimethyl-8,9-dihydro-4H-furo[2,3-h]chromen-4-one;

(S)-3,5,7-trihydroxy-2-(4-hydroxyphenyl)-6-((2,6,6-trimethylcyclohex-2-en-1-yl)methyl)-4H-chromen-4-one;

(S)-2-(3,4-dihydroxy-2-((2,6,6-trimethylcyclohex-2-en-1-yl)methyl)phenyl)-5,7-dihydroxy-3-methoxy-4H-chromen-4-one;

5,7-dihydroxy-2-((4aS,9aR)-5-hydroxy-1,1,4a-trimethyl-2,4a,9,9a-tetrahydro-1H-xanthen-8-yl)-3-methoxy-4H-chromen-4-one;

(R)-2-(3,4-dihydroxyphenyl)-6-((2,2-dimethyl-6-methylenecyclohexyl)methyl)-5,7-dihydroxy-4H-chromen-4-one;

(R)-2-(3,4-dihydroxyphenyl)-6-((2,2-dimethyl-6-methylenecyclohexyl)methyl)-5-hydroxy-7-methoxy-4H-chromen-4-one;

(7aS,11aR)-3-(3,4-dihydroxyphenol)-6-methoxy-8,8,11a-trimethyl-7a,9,10,11-tetrahydro--7H-pyrano[2,3-c]xanthen-1-one;

1,3,7,8-tetrahydroxy-6-((2,6,6-trimethylcyclohex-2-en-1-yl)methyl)-11H-benzofuro[3,2-b]chromen-11-one;

3,5,7-trihydroxy-2-((4aS,9aR)-5-hydroxy-1,1,4a-trimethyl-2,3,4,4a,9,9a-hexahydro-1H-xanthen-8-yl)-4H-chromen-4-one;

(4aS,15aR)-6,10,12-trihydroxy-1,1,4a-trimethyl-2,4a,15,15a-tetrahydrochromeno[2',3':4,5]furo[3,2-a]xanthen-9(1H)-one;

(S)-2-(3,4-dihydroxyphenyl)-5,7-dihydroxy-6-((2,6,6-trimethylcyclohex-2-en-1-yl)methyl)-4H-chromen-4-one;

2-(3,4-dihydroxyphenyl)-5,7-dihydroxy-6-(((1S,5S)-5-hydroxy-2,2-dimethyl-6-methylenecyclohexyl)methyl)-4H-chromen-4-one;

2-(3,4-dihydroxyphenyl)-5,7-dihydroxy-6-(((1S)-2-hydroxy-2,6,6-trimethylcyclohexyl)methyl)-4H-chromen-4-one;

(7aR,11aS)-3-(3,4-dihydroxyphenyl)-6-hydroxy-8,8,11a-trimethyl-7a,8,9,10,11,11a-hexahydro-1H,7H-pyrano[2,3-c]xanthen-1-one;

7-(3,4-dihydroxyphenyl)-4-hydroxy-2,3,3-trimethyl-2,3-dihydro-5H-furo[3,2-g]chromen-5-one; and (6aS,10aR)-2-(3,4-dihydroxyphenyl)-5-hydroxy-7,7,10a-trimethyl-6a,7,8,9,10,10a-hexahydro-4H,6H-pyrano[3,2-b]xanthen-4-one.

Still another aspect of the present disclosure is to provide a pharmaceutical composition comprising the aforesaid *Helminthostachys zeylanica*, ugonins, compounds of formula (I) or their pharmaceutically acceptable salts, which is useful for the treatment or prevention of metabolic diseases, such as treating or preventing various diet-associated metabolic diseases, including metabolic syndrome, lipid metabolism disorder and carbohydrate metabolism disorder.

Delivery forms of the pharmaceutical compositions containing one or more dosage units of the active agents according to the present disclosure may be prepared by using pharmaceutical excipients and compounding techniques known to those skilled in the art. The formulations of the present disclosure can be in the form of tablets, capsules, sachets, dragees, powders, granules, lozenges, powders for reconstitution, liquid preparations, or suppositories.

For oral administration, the pharmaceutical compositions of the present disclosure can be provided in the form of tablets or capsules, or as a solution, emulsion, or suspension.

Oral tablets may include active ingredients according to the present disclosure mixed with pharmaceutically acceptable excipients, such as inert diluents, disintegrating agents, binding agents, lubricating agents, sweetening agents, flavoring agents, coloring agents and preservative agents. Examples of suitable inert filler include sodium carbonate, calcium carbonate, sodium phosphate, calcium phosphate, lactose, starch, sugar, glucose, methyl cellulose, magnesium stearate, mannitol, sorbitol, and the like.

Capsules for oral administration include hard and soft gelatin capsules. To prepare hard gelatin capsules, active ingredients of the present disclosure may be mixed with a solid, semi-solid, or liquid diluent. Soft gelatin capsules may be prepared by mixing the active ingredients of the present disclosure with water, an oil such as peanut oil or olive oil, liquid paraffin, a mixture of mono- and di-glycerides of short chain fatty acids, polyethylene glycol 400, or propylene glycol.

Liquids for oral administration may be in the form of suspensions, solutions, emulsions or syrups or lyophilized or presented as a dry product for reconstitution with water or other suitable vehicle before administration.

Such liquid compositions may optionally contain pharmaceutically-acceptable excipients such as suspending agents (e.g. sorbitol, methyl cellulose, sodium alginate, gelatin, hydroxyethyl cellulose, carboxymethyl cellulose, aluminum stearate gel and the like); non-aqueous vehicles such as oil (e.g. almond oil or coconut oil), propylene glycol, ethanol, or water; preservatives (e.g. methyl or propyl p-hydroxybenzoate or sorbic acid); wetting agents such as lecithin; and flavoring agents or coloring agents.

Example: Preparation of *Helminthostachys zeylanica* Extract

*Helminthostachys zeylanica* (*H. zeylanica*, or HZ) was purchased from a traditional Chinese herbal medicine provider. The plant was identified by comparison with the voucher specimen (NRICM-99-003) already deposited at the herbarium of National Research Institute of Chinese Medicine, Republic of China. The rhizomes of *H. zeylanica* (531 g) were heated under reflux with 2.5 L EtOH—$H_2O$=1:1 (2.5 L×3) for one hour; the filtrate was concentrated and lyophilized to afford HZ extract (29 g).

Example: Preparation of Ugonins

HZ extract thus obtained was subject to HPLC purification to obtain for example ugonin K, ugonin O, ugonin M, ugonin J, etc. In addition, ugonin L, ugonin T and other ugonins may be prepared according to known methods. Various ugonins described in the present disclosure, such as ugonin A to ugonin U, a total of 21 ugonins, can also be prepared or isolated by a person skilled in the art and are therefore not described in detail for brevity.

Example: Preparation of Experimental Animals

Thirty 4-week-old male C57BL/6J mice were obtained from BioLASCO Taiwan Co, Ltd. All mice were individually housed under a constant temperature and 12-hour light/dark cycle according to standard animal laboratory conditions and subsequently divided randomly into three groups and fed a normal diet (ND group, n=10), high-fat diet (HFD group, n=10, feed containing 30 wt % fat and 1 wt % cholesterol), or HFD with 0.5 wt % (weight for weight) *Helminthostachys zeylanica* extract (HZ group, n=10) for 12 weeks.

At the end of the experimental period, all mice were anesthetized after a 12-hour fast; blood was taken from the inferior vena cava to determine the glucose, plasma lipid, and enzyme concentrations. The liver and adipose tissue were removed according to conventional protocols, rinsed with physiological saline, weighed, immediately frozen in liquid nitrogen, and stored until analysis.

Figure 1B:
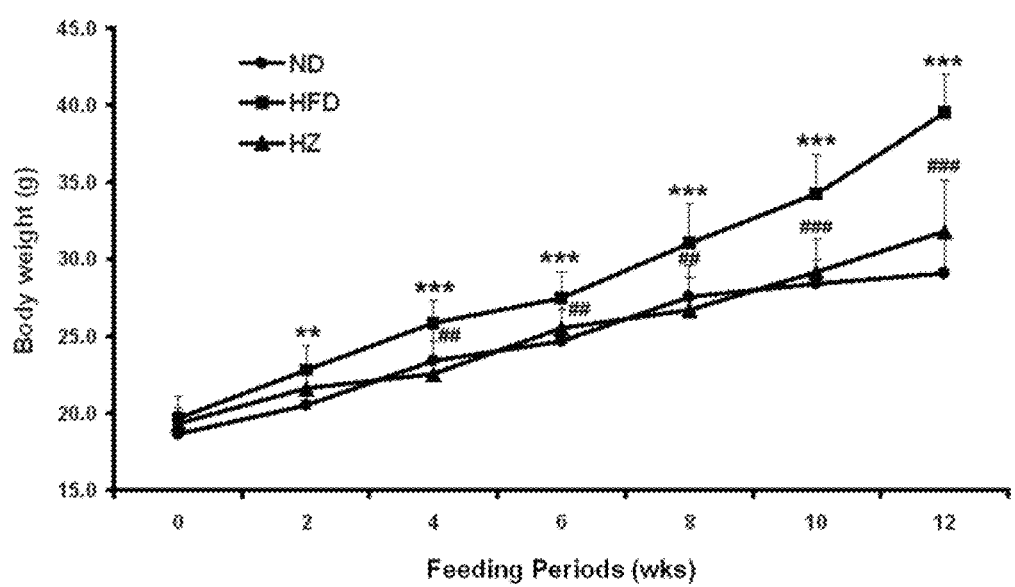
FIG. 1B illustrates changes in body weight of mice.
Figure 1C:
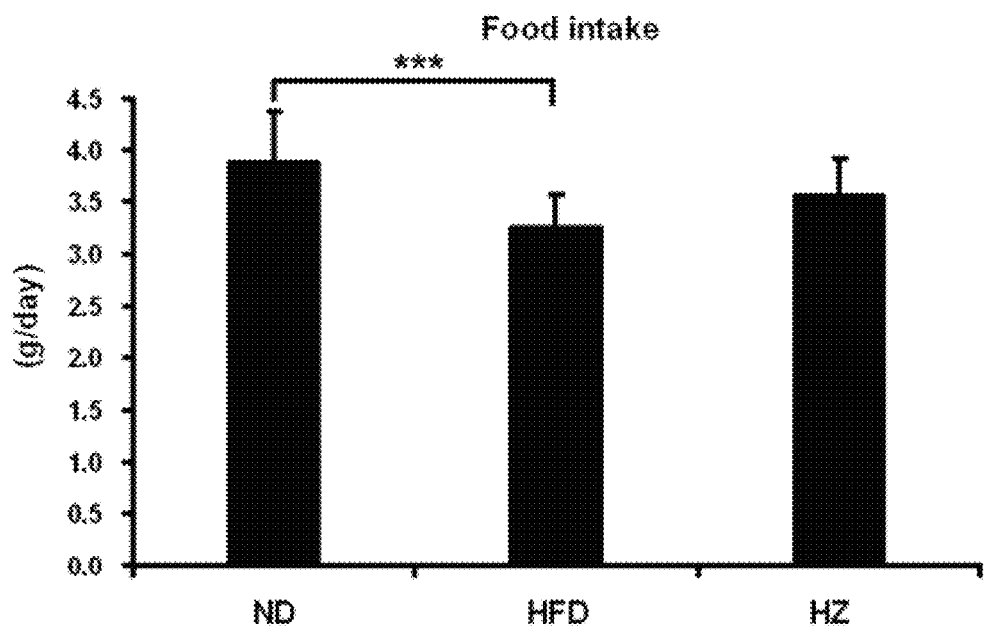
FIG. 1C illustrates daily food intake of mice.
Figure 1D:
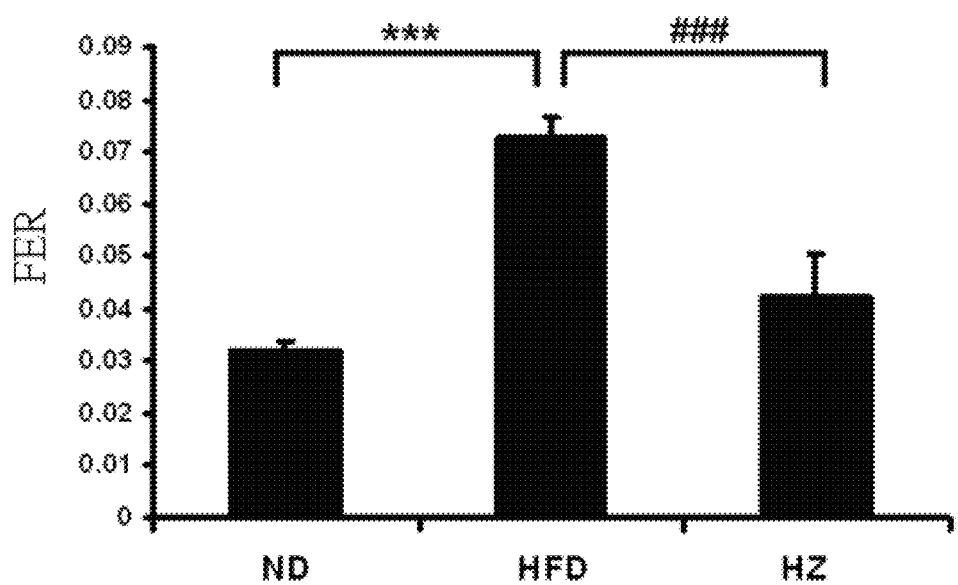
FIG. 1D illustrates food efficiency ratio of mice.

FIG. 1A shows changes in body shape and waistline of mice after 12 weeks; FIG. 1B illustrates changes in body weight of mice during 12 weeks; FIG. 1C illustrates daily food intake of mice; and FIG. 1D illustrates food efficiency ratio (FER=increase in body weight/food intake) of mice. From FIG. 1A to FIG. 1D, it can be observed that *Helminthostachys zeylanica* extract is useful for body weight control, obesity inhibition and FER reduction, and *Helminthostachys zeylanica* extract does not significantly affect food intake or appetite.

Example: Morphology Observation of Liver and Fat Tissues

The liver and epididymal adipose tissue (EAT) were fixed in 10% (volume for volume) paraformaldehyde/PBS and embedded in paraffin for staining with hematoxylin and eosin; the stained area was visualized using a microscope set at a 200-fold magnification.

Figure 2A:
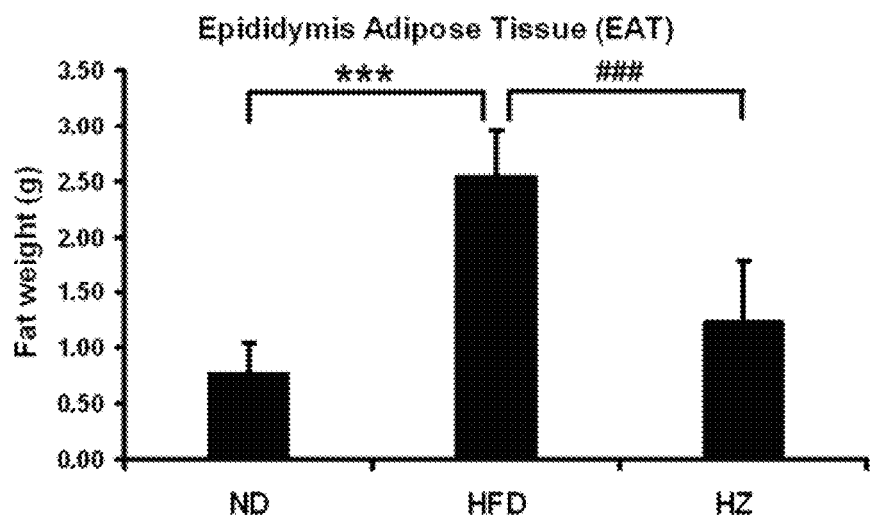
FIG. 2A illustrates the weight of adipose tissue of mice.
Figure 2B:
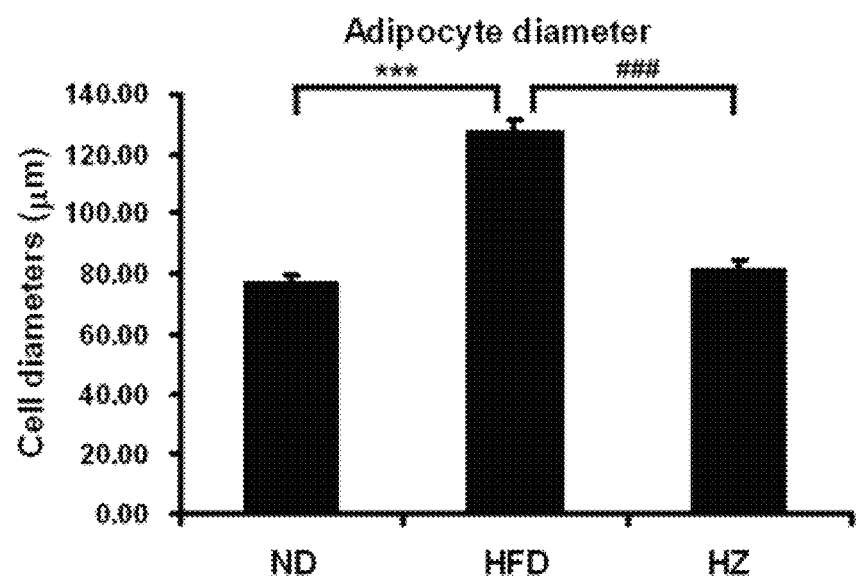
FIG. 2B illustrates the measurements of adipocyte diameter.
Figure 2C:
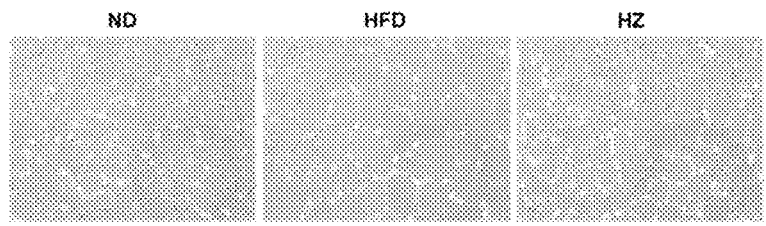
FIG. 2C shows the microscopic pictures of adipocytes.

FIG. 2A illustrates the weight of adipose tissue of mice; FIG. 2B illustrates the measurements of adipocyte diameter; and FIG. 2C shows the microscopic pictures of adipocytes. From FIG. 2A to FIG. 2C, it can be observed that *Helminthostachys zeylanica* extract is beneficial for the reduction of fat tissue weight and control of adipocyte size.

Example: Hepatic and Plasma Lipid

The total plasma triglyceride (TG), total cholesterol (TC), HDL cholesterol (HDLC), glutamic oxaloacetic transaminase (GOT), glutamic pyruvic transaminase (GPT), and Lipase (LIP) levels were measured using enzymatic assay kits by FUJI DRI-CHEM analyser, and the non-HDL cholesterol level was calculated as [(total cholesterol)−(HDLC)−(TG/5)].

Figure 3:
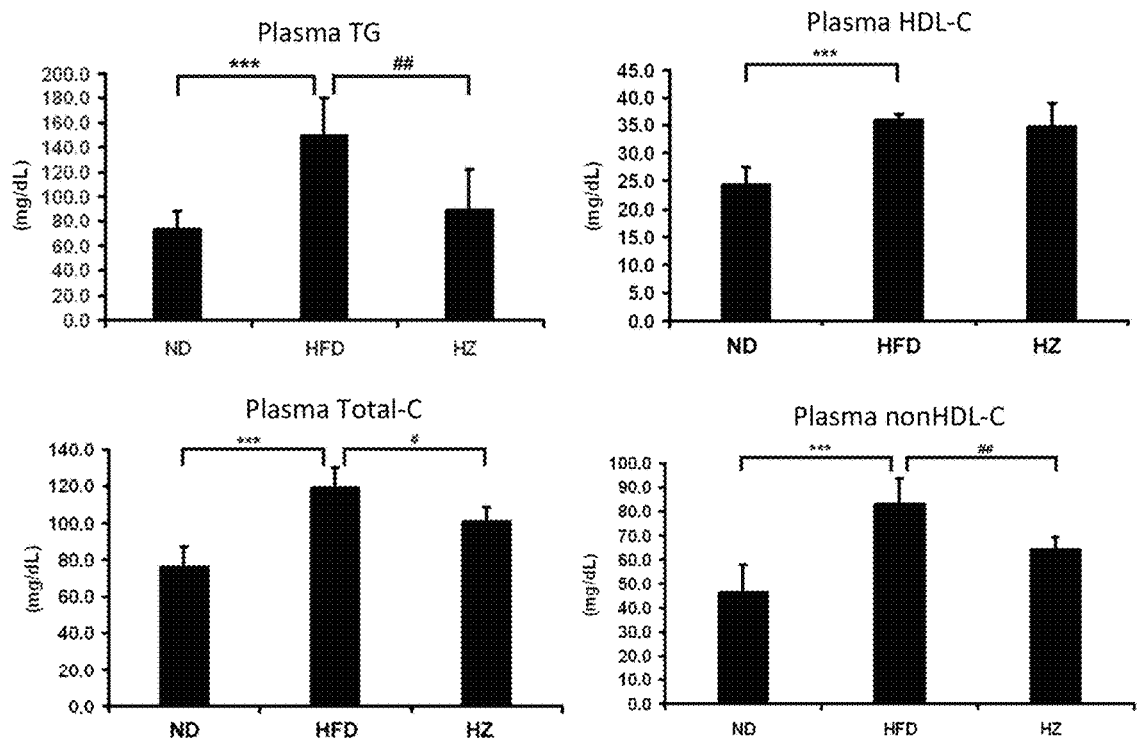
FIG. 3 illustrates plasma triglyceride level (TG), total cholesterol level (TC), HDL cholesterol level (HDLC) and non-HDL cholesterol level of mice.

FIG. 3 illustrates plasma triglyceride level (TG), total cholesterol level (TC), HDL cholesterol level (HDLC) and non-HDL cholesterol level of mice. It can be observed that *Helminthostachys zeylanica* extract is beneficial for the reduction of TG level, TC level and non-HDL cholesterol level, and its influence on HDL cholesterol is less significant.

Figure 4A:
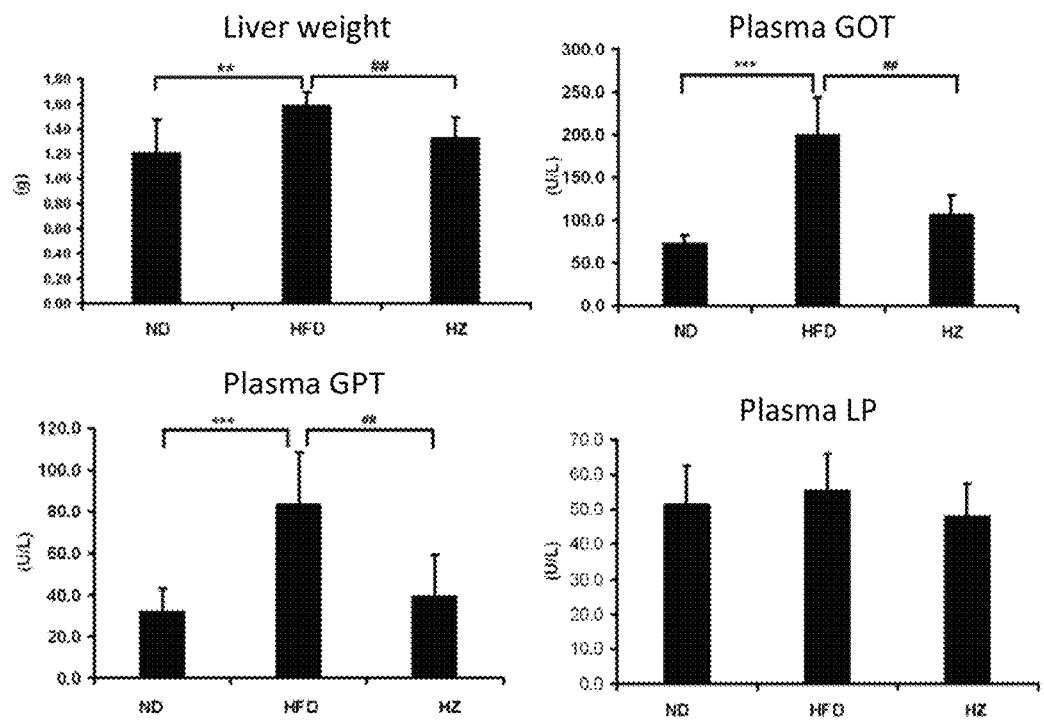
FIG. 4A illustrates liver weight of mice, GOT, GPT and LIP.
Figure 4B:
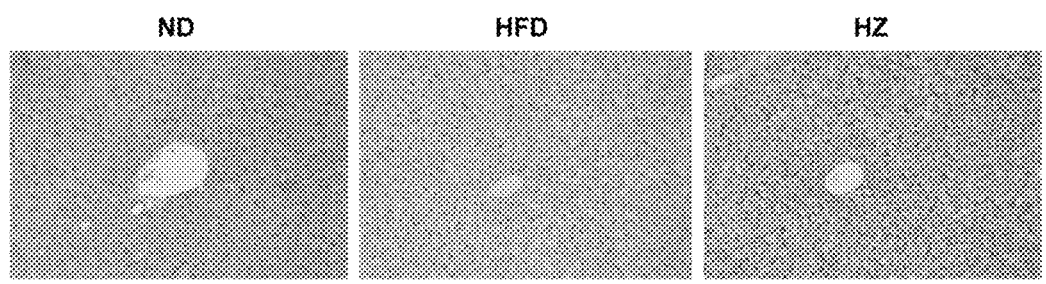
FIG. 4B shows staining pictures of transverse liver.

FIG. 4A shows the liver weight, GOT, GPT and LIP of each group of mice. As shown, *Helminthostachys zeylanica* extract is useful for the control or inhibition of liver weight increase; mice in HZ group (experimental group) have significantly lower GOT and GPT, and the kidney enzyme LIP level is not significantly changed, indicating that *Helminthostachys zeylanica* extract is not nephrotoxic. As shown in FIG. 4B, tissue morphology analysis also revealed that the accumulation of hepatic lipid droplets was decreased in the HZ group compared with the HFD group.

Example: Blood Glucose, Plasma Insulin and HOMA-IR

Every 2 weeks, the 12-hour fasting blood glucose was measured in tail vein blood with a glucose analyzer; enzymatic assay was used to measure the plasma insulin concentration, and the homeostasis model assessment of insulin resistance (HOMA-IR) was calculated as [fasting insulin concentration (mU/L)×fasting glucose concentration (mg/dL)×0.05551]/22.5.

Figure 5:
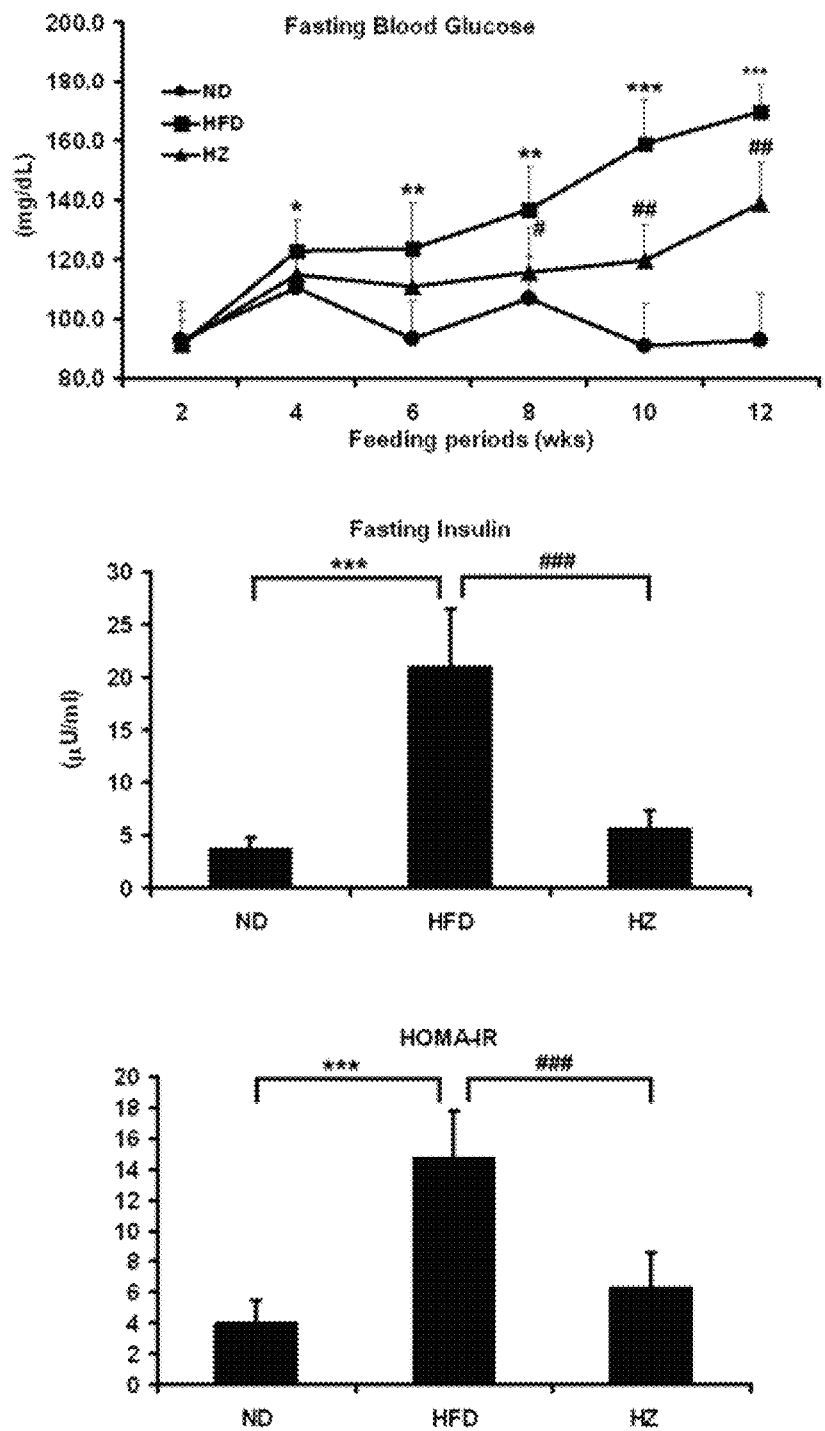
FIG. 5 illustrates fasting blood glucose level, fasting plasma insulin level, and HOMA-IR index.

FIG. 5 illustrates fasting blood glucose level, fasting plasma insulin level, and HOMA-IR index. It can be observed that HZ group shows a fasting blood glucose level significantly lower than the HFD group from the sixth week; in addition, the fasting insulin level and HOMA-IR index are significantly lower, indicating the decrease of insulin resistance.

Example: Human Hepatocyte Culture and Treatment

Human hepatocytes were maintained in a primary hepatocyte medium, and palmitate of different concentrations was provided in the form of palmitate/BSA complex to induce fatty acid overload, so as to observe the effects of *Helminthostachys zeylanica* extract and ugonins on the hepatocytes. To measure intracellular lipid content, human hepatocytes were stained using the Oil Red O method according to the protocol known in the art, and light absorbance at 510 nm was measured to calculate intracellular lipid content.

Figure 6A:
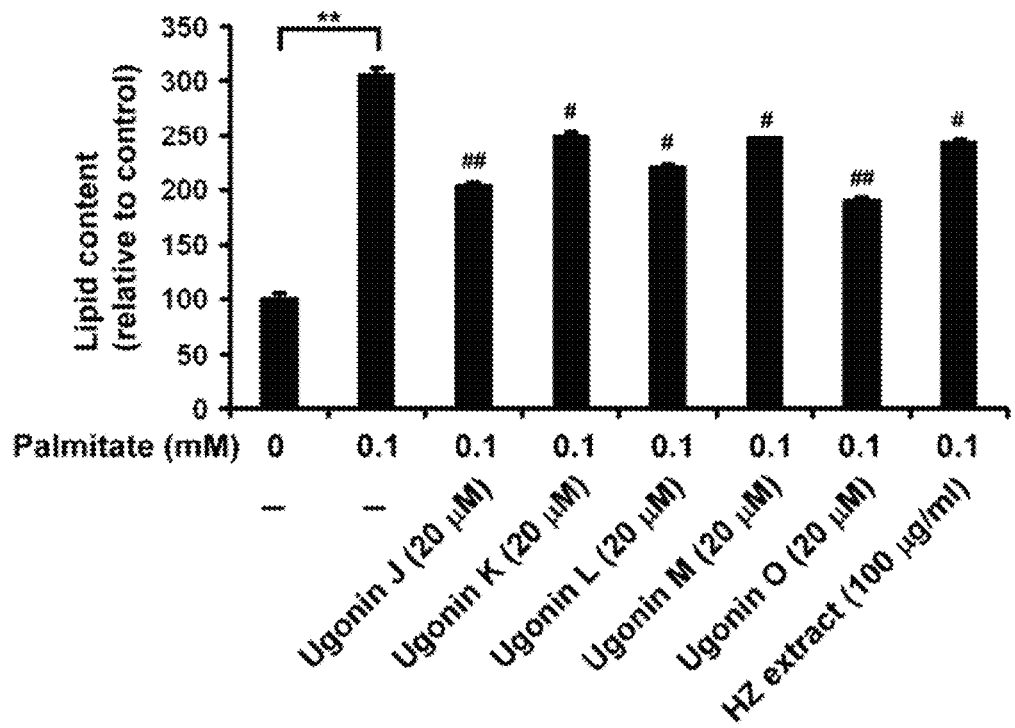
FIG. 6A shows the effect of ugonins and *Helminthostachys zeylanica* extract on palmitate-induced lipid accumulation.
Figure 6B:
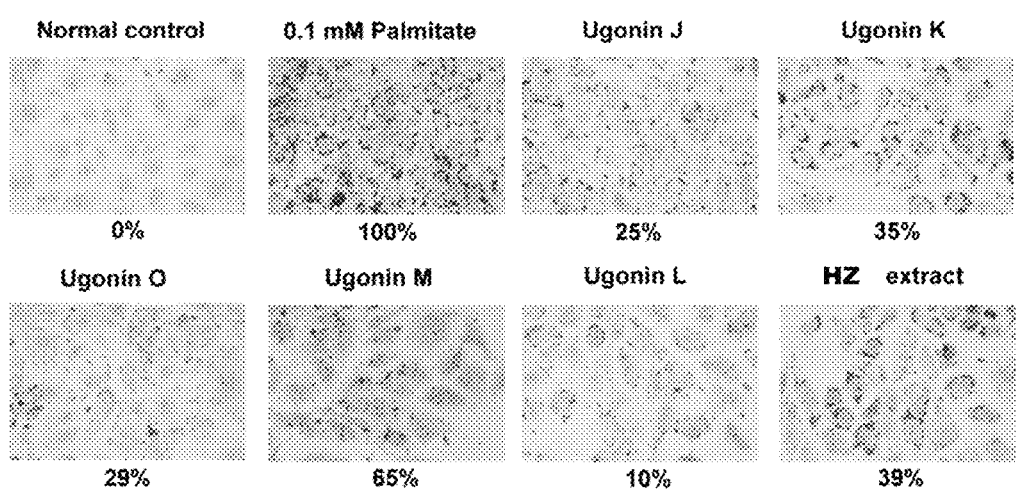
FIG. 6B shows Oil-Red O staining pictures of human hepatocytes.

FIG. 6A shows the effect of ugonins and *Helminthostachys zeylanica* extract on palmitate-induced lipid accumulation, and FIG. 6B shows Oil-Red 0 staining pictures of human hepatocytes, both indicating that *Helminthostachys zeylanica* extract and ugonins demonstrate significant inhibition of lipid accumulation at 100 μg/ml and 20 μM respectively.

Example: PPAR-γ Transcriptional Activity

The transcriptional activity of PPAR-γ was assessed using the purchased transcription factor assay kit, and absorbance of the developed color was read at 450 nm to evaluate the effect of ugonins on PPAR-γ.

Figure 7:
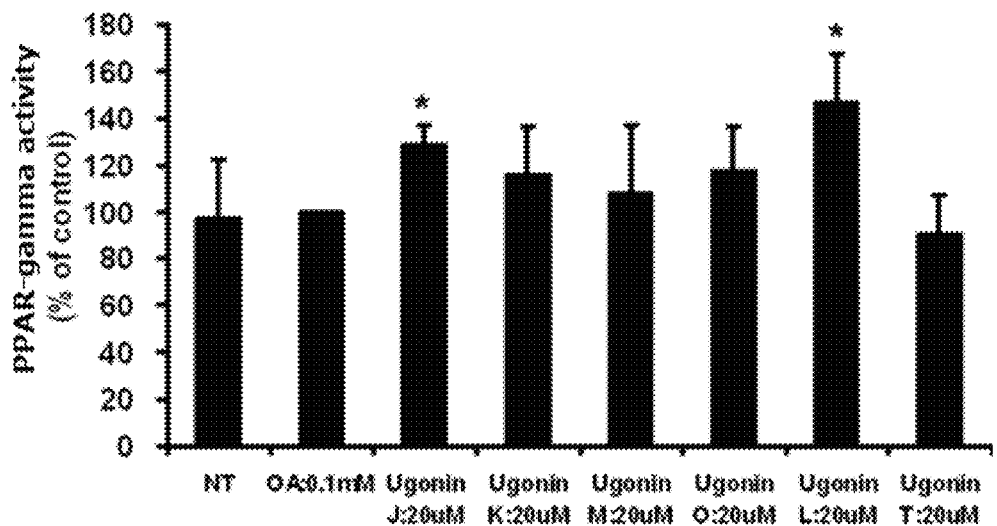
FIG. 7 illustrates the effect of various ugonins on PPAR-γ activity.

FIG. 7 illustrates the effect of various ugonins on PPAR-γ activity, wherein most ugonins enhance PPAR-γ activity at the concentration of 20 μM. PPAR-γ is primarily expressed in adipose tissue and identified as a regulator of adipogenesis. Some PPAR-γ agonists, such as thiazolidinediones (TZDs), lower the hyperglycemia, hyperinsulinemia and hypertriglyceridemia found in type 2 diabetic subjects. Therefore, the results of FIG. 7 evidence the beneficial effects of ugonins on treatment or prevention of lipid metabolism disorder or carbohydrate metabolism disorder.

Example: Akt Kinase Activity Assay

Akt kinase activity was determined by commercial Akt assay kit according to the manufacturer's directions. Phosphorylation states of GSK3-α were determined by Western blotting, so as to evaluate the effect of various ugonins on Akt activity.

Figure 8:
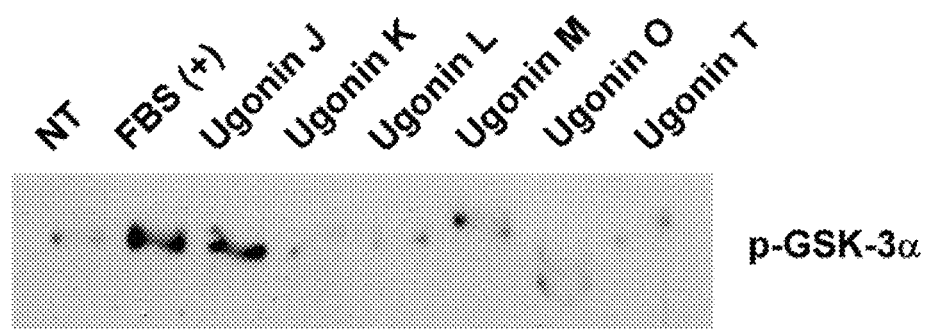
FIG. 8 illustrates the effect of various ugonins on Akt activity.

FIG. 8 shows the results of Western blotting from Akt assay kit, which reveal the effect of various ugonins on Akt activity. The results indicate that ugonins, particularly ugonin J, promote Akt activity and are therefore beneficial to blood glucose regulation.

Example: AMPK Activation Test

AMP-activated protein kinase (AMPK) is a critical regulator of fatty acid oxidation. The activation of AMPK by phosphorylation of Thr-172 switches off fatty acid synthesis. Some anti-diabetic drugs, such as metformin and thiazolidinediones, alleviate fatty liver in humans by downregulating lipid metabolism through AMPK activation.

Figure 9A:
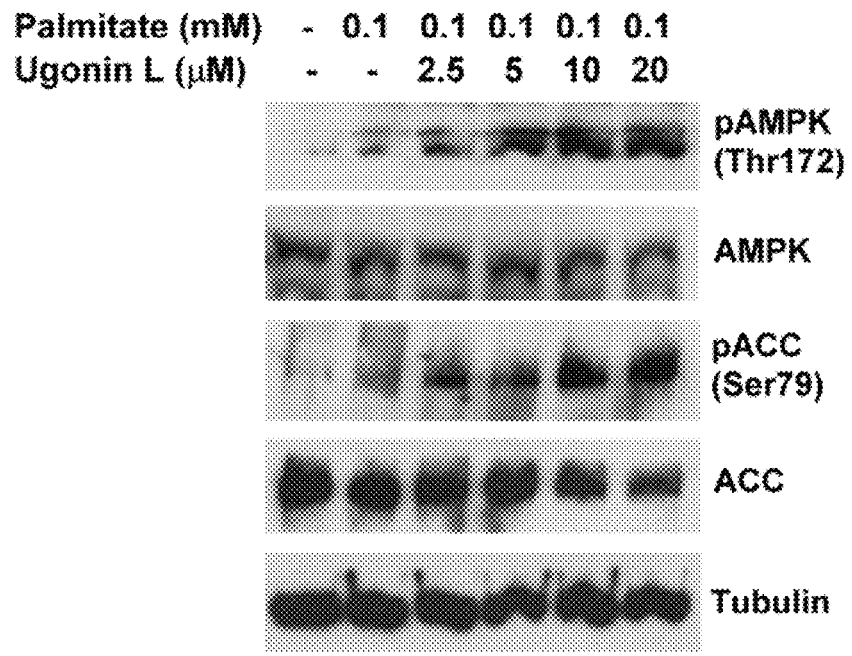
FIG. 9A illustrates the effect of ugonin L on human hepatocyte AMPK activity.
Figure 9B:
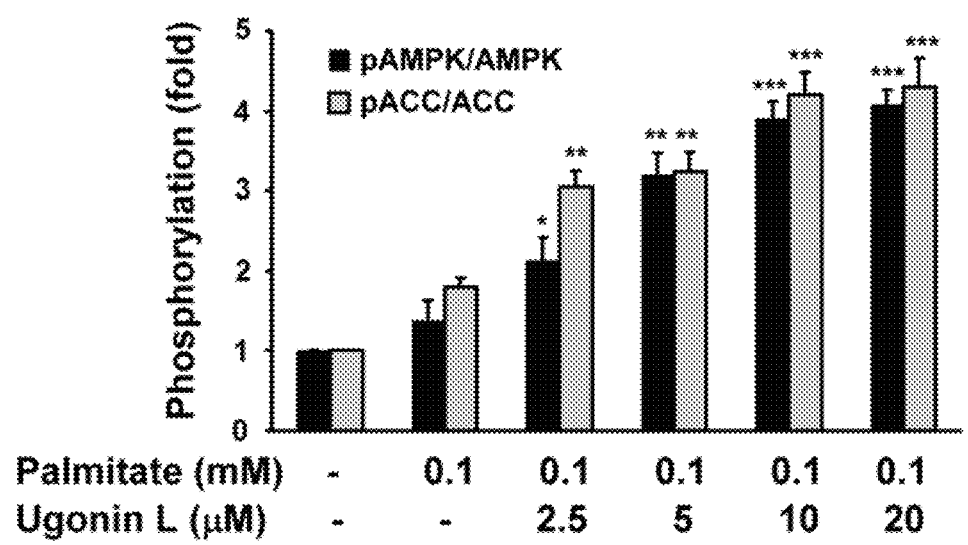
FIG. 9B illustrates phosphorylation level of AMPK and ACC.

Human hepatocytes were incubated in PH medium alone (control group) or containing 0.1 mM palmitate in the presence or absence of 0, 2.5, 5, 10 and 20 μM of ugonin L to determine whether ugonin L increases phospho-AMPK levels by Western blotting. FIG. 9A is the result of Western blotting of AMPK, which illustrates the effect of ugonin L on human hepatocyte AMPK activity, and FIG. 9B illustrates phosphorylation level of AMPK and ACC, showing that 2.5, 5, 10 or 20 μM of ugonin L significantly increases AMPK phosphorylation, and the increased AMPK phosphorylation is accompanied by a significant increase in ACC phosphorylation at Ser-79, indicating that ugonin L-induced activation of AMPK leads to inhibition of ACC.

Example: Glucose Stimulated Insulin Secretion

The clonal rat pancreatic β-cell line (BRIN-BD11) was grown as a monolayer in culture dishes at 37° C. under 5% $CO_2$/air with 90% humidity. Cells were maintained in RPMI 1640 medium containing 10% foetal bovine serum and 5% penicillin and streptomycin mixture.

BRIN-BD11 cells were plated on 24-well plates ($0.5 \times 10^5$ cells/well) and incubated for 48 hours with media containing 5.6 mM glucose. Before performing acute insulin secretion test, cells were pre-incubated with 1.1 mM glucose in Krebs-Ringer Bicarbonate Buffer for 45 min at 37° C. Then, cells were challenged with vehicle (DMSO) or various ugonins in 16.7 mM glucose in Krebs-Ringer Bicarbonate Buffer for 20 min. The media were collected for insulin determination. Insulin concentrations were quantified by the Homogeneous Time-Resolved Fluorescence (HTRF) insulin assay and normalized to a million of total cell numbers.

Data were presented as mean±standard error of the mean. Statistical analyses were performed using GraphPad Prism (GraphPad, CA, USA). Single parameter-based comparisons were obtained from the unpaired student's t-test. P values less than 0.05 and 0.01 were considered to be significant.

Figure 10:
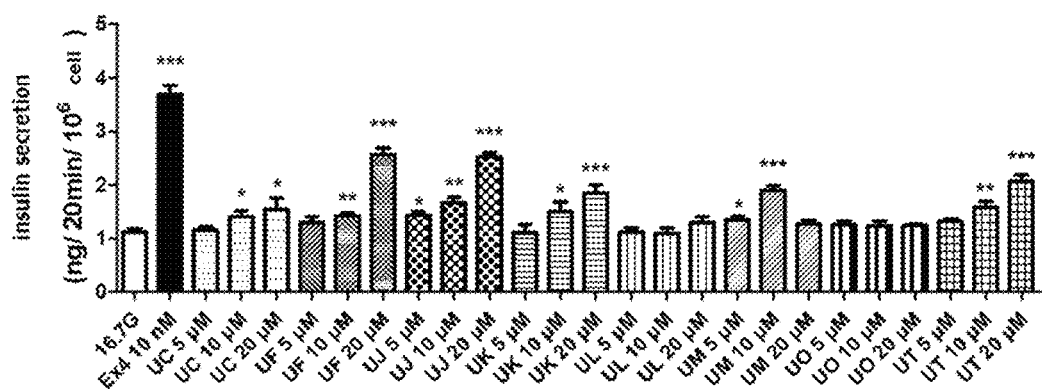
FIG. 10 illustrates potential insulinotropic effects of ugonins on glucose stimulated insulin secretion of BRIN-BD11 cells.

As shown in FIG. 10, by employing glucose responsive insulin secreting cell line BRIN-BD11, potential insulinotropic effects of ugonins on glucose stimulated insulin secretion of BRIN-BD11 cells were evaluated. Exendin-4 (EX-4) was served as a positive control as an potent insulinotropic drug. As a result, ugonin C, F, J, K, M, and T below the concentration of 20 μM can significantly enhance insulin secretion of BRIN-BD11 cells in the presence of 16.7 mM glucose (hyperglycemic condition).

According to the above descriptions, exemplary embodiments and examples are provided to elaborate the concept of the present disclosure. However, skilled artisans appreciate that other aspects and embodiments as well as various modifications are possible without departing from the scope defined by the claims. Therefore, the detailed descriptions above shall be applied in an illustrative manner but not limiting manner when construing the claims, and various changes, variations and modifications shall all be encompassed by the scope of the claims.

Furthermore, certain features described in the embodiments can be provided in a single embodiment alone or in combination, and different embodiments can be presented individually or as any sub-combination. It is to be understood that a range should be interpreted flexibly to include not only the numerical values explicitly recited but also to include all the individual numerical values or sub-ranges encompassed within that range as if each numerical value and sub-range are explicitly recited.

What is claimed is:

1. A method of using *Helminthostachys zeylanica* for the treatment of a metabolic disease, comprising a step of administering to a recipient in need thereof a therapeutically effective amount of an extract of the *Helminthostachys zeylanica*, wherein the metabolic disease includes metabolic syndrome, lipid metabolism disorder or carbohydrate metabolism disorder.

2. The method of claim 1, wherein the extract is an alcoholic extract of rhizome.

3. The method of claim 1, wherein the lipid metabolism disorder is selected from the group consisting of excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease and a combination thereof.

4. The method of claim 1, wherein the carbohydrate metabolism disorder is selected from the group consisting of hyperglycemia, hyperinsulinemia, diabetes mellitus type 2, insulin resistance, insulin disorder, impaired glucose tolerance and a combination thereof.

5. A method of using a ugonin for the treatment, inhibition or alleviation of a diet-induced metabolic disease, comprising a step of administering to a recipient in need thereof a therapeutically effective amount of the ugonin.

6. The method of claim 5, wherein the ugonin is selected from the group consisting of ugonin J, ugonin K, ugonin L, ugonin M, ugonin O, ugonin T and a combination thereof.

7. A method of using a ugonin for the treatment of a metabolic disease mediated by PPAR-γ, Akt, AMPK, ACC, SREBP1, FAS, FOXO1, CPT1 or ATGL, comprising a step of administering to a recipient in need thereof a therapeutically effective amount of the ugonin, wherein the metabolic disease is selected from the group consisting of metabolic syndrome, excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease, hyperglycemia, hyperinsulinemia, diabetes mellitus type 2, insulin resistance, insulin disorder, impaired glucose tolerance and a combination thereof.

8. A method of using a compound of formula (I) or its pharmaceutically acceptable salt for the treatment of a metabolic disease, comprising a step of administering to a recipient in need thereof a therapeutically effective amount of the compound of formula (I) or its pharmaceutically acceptable salt,

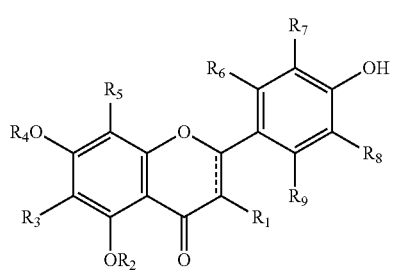

(I)

wherein

⫶ represents a single bond or a double bond;

$R_1$ is selected from H, OH and $(C_1-C_6)$alkoxy or $R_1$ and $R_9$ form an oxygen-containing heterocyclic ring;

$R_2$ is H or $R_2$ and $R_3$ form an oxygen-containing heterocyclic ring;

$R_3$ is selected from H and substituted or unsubstituted $(C_1-C_6)$alkylene$(C_3-C_6)$cyclohydrocarbyl, or $R_3$ and $R_2$ form an oxygen-containing heterocyclic ring or $R_3$ and $R_4$ form an oxygen-containing heterocyclic ring;

$R_4$ is selected from H and $(C_1-C_6)$alkyl, or $R_4$ and $R_3$ form an oxygen-containing heterocyclic ring or $R_4$ and $R_5$ form an oxygen-containing heterocyclic ring;

$R_5$ is selected from H and $(C_1-C_6)$alkyl-substituted $(C_2-C_6)$alkenyl or $R_5$ and $R_4$ form an oxygen-containing heterocyclic ring;

$R_6$ is selected from H and substituted or unsubstituted $(C_1-C_6)$alkylene$(C_3-C_6)$ cyclohydrocarbyl or $R_6$ and $R_7$ form an oxygen-containing heterocyclic ring;

$R_7$ is selected from H, OH and $(C_1-C_6)$alkoxy or $R_7$ and $R_6$ form an oxygen-containing heterocyclic ring;

$R_8$ is selected from H and OH; and $R_9$ is H or $R_9$ and $R_1$ form an oxygen-containing heterocyclic ring, wherein the metabolic disease includes metabolic syndrome, lipid metabolism disorder or carbohydrate metabolism disorder.

9. The method of claim 8, wherein $R_1$ is selected from H, OH and $(C_1-C_6)$alkoxy; $R_2$ is H; $R_3$ is selected from H or substituted or unsubstituted $(C_1-C_3)$alkylene$(C_5-C_6)$ cyclohydrocarbyl; $R_4$ is selected from H and $(C_1-C_3)$alkyl or $R_4$ and $R_5$ form an oxygen-containing heterocyclic ring; $R_5$ is selected from H and $(C_1-C_3)$alkyl$(C_2-C_4)$ alkenyl; $R_6$ is H; $R_7$ is selected from H, OH and $(C_1-C_6)$alkoxy; $R_8$ is selected from H and OH; and $R_9$ is H.

10. The method of claim 8, wherein the compound of formula (I) is selected from the group consisting of:
2-(3,4-dihydroxyphenyl)-5-hydroxy-12,12-dimethyl-8, 8a,9,10,11,12,12a,13-octahydro-4H-benzo[5,6]oxepino[2,3-h]chromen-4-one;
5-hydroxy-2-(4-hydroxy-3-methoxyphenyl)-12,12-dimethyl-8,8a,9,10,11,12,12a,13-octahydro-4H-benzo[5,6]oxepino[2,3-h]chromen-4-one;
5-hydroxy-2-(4-hydroxyphenyl)-3-methoxy-8,9,9-trimethyl-8,9-dihydro-4H-furo[2,3-h]chromen-4-one;
5-hydroxy-2-(4-hydroxyphenyl)-8,9,9-trimethyl-2,3,8,9-tetrahydro-4H-furo[2,3-h]chromen-4-one;
(R)-5,7-dihydroxy-2-(4-hydroxyphenyl)-8-(2-methylbut-3-en-2-yl)chromen-4-one;
3,5-dihydroxy-2-(4-hydroxyphenyl)-8,9,9-trimethyl-8,9-dihydro-4H-furo[2,3-h]chromen-4-one;
(S)-3,5,7-trihydroxy-2-(4-hydroxyphenyl)-6-((2,6,6-trimethylcyclohex-2-en-1-yl)methyl)-4H-chromen-4-one;
(S)-2-(3,4-dihydroxy-2-((2,6,6-trimethylcyclohex-2-en-1-yl)methyl)phenyl)-5,7-dihydroxy-3-methoxy-4H-chromen-4-one;
5,7-dihydroxy-2-((4aS,9aR)-5-hydroxy-1,1,4a-trimethyl-2,4a,9,9a-tetrahydro-1H-xanthen-8-yl)-3-methoxy-4H-chromen-4-one;
(R)-2-(3,4-dihydroxyphenyl)-6-((2,2-dimethyl-6-methylenecyclohexyl)methyl)-5,7-dihydroxy-4H-chromen-4-one;
(R)-2-(3,4-dihydroxyphenyl)-6-((2,2-dimethyl-6-methylenecyclohexyl)methyl)-5-hydroxy-7-methoxy-4H-chromen-4-one;
(7aS,11aR)-3-(3,4-dihydroxyphenyl)-6-methoxy-8,8,11a-trimethyl-7a,9,10,11-tetrahydro-7H-pyrano[2,3-c]xanthen-1-one;
1,3,7,8-tetrahydroxy-6-((2,6,6-trimethylcyclohex-2-en-1-yl)methyl)-11H-benzofuro[3,2-b]chromen-11-one;
3,5,7-trihydroxy-2-((4aS,9aR)-5-hydroxy-1,1,4a-trimethyl-2,3,4,4a,9,9a-hexahydro-1H-xanthen-8-yl)-4H-chromen-4-one;
(4aS,15aR)-6,10,12-trihydroxy-1,1,4a-trimethyl-2,4a,15,15a-tetrahydrochromeno[2',3':4,5]furo[3,2-a]xanthen-9(1H)-one;
(S)-2-(3,4-dihydroxyphenyl)-5,7-dihydroxy-6-((2,6,6-trimethylcyclohex-2-en-1-yl)methyl)-4H-chromen-4-one;
2-(3,4-dihydroxyphenyl)-5,7-dihydroxy-6-(((1S,5S)-5-hydroxy-2,2-dimethyl-6-methylenecyclohexyl)methyl)-4H-chromen-4-one;

2-(3,4-dihydroxyphenyl)-5,7-dihydroxy-6-(((1S)-2-hydroxy-2,6,6-trimethylcyclohexyl)methyl)-4H-chromen-4-one;
(7aR,11aS)-3-(3,4-dihydroxyphenyl)-6-hydroxy-8,8,11a-trimethyl-7a,8,9,10,11,11a-hexahydro-1H,7H-pyrano[2,3-c]xanthen-1-one;
7-(3,4-dihydroxyphenyl)-4-hydroxy-2,3,3-trimethyl-2,3-dihydro-5H-furo[3,2-g]chromen-5-one;
(6aS,10aR)-2-(3,4-dihydroxyphenyl)-5-hydroxy-7,7,10a-trimethyl-6a,7,8,9,10,10a-hexahydro-4H,6H-pyrano[3,2-b]xanthen-4-one;
and a combination thereof.

11. The method of claim 8, wherein the compound of formula (I) is selected from the group consisting of:
(R)-2-(3,4-dihydroxyphenyl)-6-((2,2-dimethyl-6-methylenecyclohexyl)methyl)-5,7-dihydroxy-4H-chromen-4-one;
(R)-2-(3,4-dihydroxyphenyl)-6-((2,2-dimethyl-6-methylenecyclohexyl)methyl)-5-hydroxy-7-methoxy-4H-chromen-4-one;
(7aS,11aR)-3-(3,4-dihydroxyphenyl)-6-methoxy-8,8,11a-trimethyl-7a,9,10,11-tetrahydro-7H-pyrano[2,3-c]xanthen-1-one;
1,3,7,8-tetrahydroxy-6-((2,6,6-trimethylcyclohex-2-en-1-yl)methyl)-11H-benzofuro[3,2-b]chromen-11-one;
(4aS,15aR)-6,10,12-trihydroxy-1,1,4a-trimethyl-2,4a,15,15a-tetrahydrochromeno[2',3':4,5]furo[3,2-a]xanthen-9(1H)-one;
7-(3,4-dihydroxyphenyl)-4-hydroxy-2,3,3-trimethyl-2,3-dihydro-5H-furo[3,2-g]chromen-5-one;
and a combination thereof.

12. The method of claim 8, wherein the metabolic disease is selected from the group consisting of metabolic syndrome, excessive lipid accumulation, obesity, overweight, fatty liver, hepatic steatosis, hepatitis, cirrhosis, liver cancer, dyslipidemia, hyperlipidemia, hypertriglyceridemia, hyperlipoproteinemia, hypercholesterolemia, cardiovascular disease, hyperglycemia, hyperinsulinemia, diabetes mellitus type 2, insulin resistance, insulin disorder, impaired glucose tolerance and a combination thereof.

* * * * *